United States Patent [19]

Brassington et al.

[11] Patent Number: 4,838,253
[45] Date of Patent: Jun. 13, 1989

[54] SILICONE GEL COATED PERMEABLE WOUND DRESSING

[75] Inventors: Nigel J. Brassington, Crosshills, United Kingdom; John A. Gilbert, Henley-on-Thames, England

[73] Assignee: Johnson & Johnson, New Brunswick, N.J.

[21] Appl. No.: 64,376

[22] Filed: Jun. 22, 1987

[30] Foreign Application Priority Data

Apr. 7, 1986 [GB] United Kingdom ............... 8616418

[51] Int. Cl.$^4$ ............................................ A61L 15/00
[52] U.S. Cl. .......................... 128/156; 128/DIG. 21; 604/304; 604/358; 427/2; 428/447; 428/452
[58] Field of Search ....... 128/155, 156, 130, DIG. 21; 427/2; 428/391, 405, 447, 452; 604/304, 307, 358, 365, 367, 372, 381, 364

[56] References Cited

U.S. PATENT DOCUMENTS

| | | | |
|---|---|---|---|
| 3,042,549 | 7/1962 | Arnold et al. | 117/140 |
| 3,050,491 | 8/1962 | Nitzsche et al. | 128/156 |
| 3,697,473 | 10/1972 | Polmanteer et al. | 128/DIG. 21 |
| 4,175,557 | 11/1979 | Hung | 128/156 |
| 4,259,467 | 3/1981 | Keogh et al. | 528/12 |
| 4,373,519 | 2/1983 | Errede et al. | 128/156 |
| 4,408,996 | 10/1983 | Baldwin | 604/358 |
| 4,418,822 | 12/1983 | Dotta | 128/155 |
| 4,661,099 | 4/1987 | von Bittera et al. | 128/156 |
| 4,684,538 | 8/1987 | Klemarczyk | 427/54.1 |
| 4,684,557 | 8/1987 | Pennace et al. | 428/452 |
| 4,690,683 | 9/1987 | Chien et al. | 128/156 |

FOREIGN PATENT DOCUMENTS

| | | | |
|---|---|---|---|
| 0100148 | 2/1984 | European Pat. Off. | 128/156 |
| 0898826 | 6/1962 | United Kingdom . | |

OTHER PUBLICATIONS

Perkins et al., Burns, vol. 9, No. 3, pp. 201-204, "Silicone Gel: A New Treatment for Burn Scabs and Contractures" (1982).

Surgitek, "Implantable Silicone Plastigel", Medical Engineering Corp., Feb. 1980.

Dow Corning Center For Aid To Medical Research, The Bulletin, "Silicone Fluid for Burn Treatment", vol. 4, No. 4, 10-1962, pp. 13-16.

Primary Examiner—Richard J. Apley
Assistant Examiner—Paul Prebilic
Attorney, Agent, or Firm—Joseph J. Brindisi

[57] ABSTRACT

A wound dressing comprises, in one embodiment, a layer of apertured material, such as a cotton gauze, coated with a tacky silicone gel or a non-tacky silicone elastomer. In an alternative embodiment, the dressing has a tacky silicone gel on one surface and a non-tacky silicone elastomer on the other surface. The gel and elastomer may be formed by crosslinking a mixture of a vinyl-substituted poly(dimethylsiloxane) and a hydride-containing poly(dimethylsiloxane).

10 Claims, No Drawings

SILICONE GEL COATED PERMEABLE WOUND DRESSING

This invention relates to dressings such as wound dressings, and more particularly to dressings having a crosslinked silicone coating on a skin-contacting surface thereof.

Silicones are a group of completely synthetic polymers containing the recurring group —$SiR_2O$—, wherein R is a radical such as an alkyl, aryl, phenyl or vinyl group. The simpler silicones are oils of very low melting point, while at the other end of the scale of physical properties are highly crosslinked silicones which form rigid solids. Intermediate in physical properties between these two extremes are silicone elastomers such as gels and rubbers.

A number of different silicone preparations have been used, or proposed for use, in wound care applications. For example, an article in Polski Przeglad Chirurgiczny Vol. 43 (2), pages 205–210 (1971) describes the incorporation of a small proportion of a silicone oil into a paraffin/lanolin coating on a tulle gras dressing.

EP-A-No. 0100148 describes a medical-surgical dressing comprising a reinforced sheet of silicone elastomer foam, one of the surfaces of the sheet having a surface layer of open cell foam and the other surface having a substantially non-cellular surface skin. The dressings are said to be useful for the treatment of wounds, burns and as liners for plaster casts.

Reinforced sheets of silicone gels have also been used as dressings for burns. They are said to be effective in reducing scarring, possibly because of their rheological properties and because they release silicone oils which may have the property of softening the skin.

According to the present invention there is provided a liquid permeable dressing comprising one or more sheets of apertured material coated with a crosslinked silicone.

In one embodiment of the invention, the crosslinked silicone is a tacky gel. In this embodiment, the dressing of the invention has been found to be an excellent substitute for tulle gras dressings. Traditional tulle gras dressings such as the dressing described in British Pharmacopoeia (1980), page 915, generally consist of a layer of gauze coated with paraffin wax. Such dressings have a number of desirable properties, and for this reason have been used extensively for many years. Among these advantages are their high degree of conformability and deformability, and the fact that their tackiness makes them very easy to apply. That is to say, a tulle gras dressing applied to a wound will usually remain in place simply by adhesion of the paraffin wax to the patient's skin (or to itself in the case of a dressing wrapped around a finger, for example) while a securing bandage is applied. Tulle gras dressings are also quite inexpensive. However, tulle gras dressings do have a number of disadvantages. Principal amongst these is that, although initially non-adherent, they often become "dry" (in the sense of losing their paraffin coating) and consequently adhere to the wound to which they are applied. This effect is due to the paraffin coating becoming mobile at body temperatures and migrating into the wound or being absorbed into the backing of the dressing or bandage. In some cases, removal of a tulle gras dressing which has become dry in this way can cause considerable trauma. Indeed, it is quite common to have to soak tulle gras dressings in order to remove them. If tulle gras dressings are changed more frequently, in an attempt to avoid them becoming attached to the wound, this may delay wound healing and adds to nursing costs.

A further disadvantage of traditional tulle gras dressings is that fibres from the gauze may become incorporated in the wound, as may the paraffin coating of the dressing. Some authorities see the migration of paraffin into a wound as an undesirable effect and any paraffin found in a wound can be difficult to remove with normal aqueous wound cleansing agents. Moreover, the pores of the gauze may become occluded if the paraffin coating is too heavy or as a result of the mobility of the paraffin during use of the dressing. While occlusive dressings are appropriate in some circumstances, it is undesirable that the nursing staff should have no control over whether the dressing used is in fact occlusive.

Still further disadvantages of conventional tulle gras dressings are that they are effectively opaque and of somewhat unsightly appearance, and the paraffin can run during storage, making them particularly messy to apply.

It has now been found that by the use of tacky silicone gels the disadvantages of conventional tulle gras dressings are avoided, while their advantages are retained. In particular, tacky silicone gels provide a coating which is exceptionally non-adherent to wounds, but which is significantly self-adherent. Moreover, such gels are entirely immobile and unaffected by heat or body exudates. This means that dressings according to the invention retain their non-adherent properties even after they have been in place for a substantial period of time, for example several days. Moreover, the fibres of the gauze are effectively encapsulated by the silicone gel, so that fibre loss into the wound is virtually eliminated. Still further advantages of the dressings of the present invention are that they can be made to some degree translucent, so that the condition of the wound can to some extent be monitored without removal of the dressing.

Dressings according to the present invention may have a crosslinked silicone coating which is non-tacky. Such dressings offer an effective alternative to dressings currently available with non-adherent plastics wound contacting layers. In common with dressings according to the present invention are highly conformable and flexible, highly non-adherent, relatively inexpensive, unaffected by wound exudate and are virtually incapable of shedding fibres.

The crosslinked silicones which are used to coat the dressings of the present invention can conveniently be characterised in terms of their tensile strength, penetrability and peel strength. As the term is used herein, "tensile strength" means the maximum tensile load which can be applied (by means of a standard Instron tester) to a 5 cm wide, 3 mm thick strip of the crosslinked silicone in question. "Penetrability" is the degree to which a standard 50 g brass probe will penetrate into the silicone under its own weight in 8 seconds at ambient conditions. The probe is generally cylindrical, 5 mm in diameter, and has a part-spherical tip with a radius of curvature of 3.625 mm (i.e. the tip is a 1 mm thick segment of a sphere). "Peel strength" is the force required to peel one end of a 5 cm wide, 3 mm thick strip of the silicone from a flat stainless steel surface, with the force being applied normally to the surface.

The tacky gels which are used to form dressings suitable as substitutes for traditional tulle gras dressings generally have a tensile strength of from 50 to 400 g, a penetrability of from 5 to 50 mm and a peel strength of from 5 to 100 g. Preferably, such gels have a tensile strength of from 80 to 300 g, a penetrability of from 8 to 30 mm and a peel strength of from 10 to 50 g. Particularly preferred tacky gels have a tensile strength of from 100 to 200 g, a penetrability of from 10 to 25 mm (e.g. about 12 mm) and a peel strength of from 15 to 35 g (e.g. about 25 g).

The crosslinked silicones which are used to form non-tacky dressings are preferably rather more robust than the above-described tacky gels. They may, for example, be silicone rubbers. If silicone gels are used, they may have a tensile strength of from 100 to 600 g, a penetrability of from 1 to 10 mm, and a peel strength of from 0 to 15 g. Preferably, the non-tacky silicones are gels having a tensile strength of from 200 to 400 g, a penetrability of from 2 to 8 mm and a peel strength of from 0 to 10 g. Particularly preferred are silicones having a tensile strength of from 260 to 330 g, a penetrability of from 4 to 7 mm and a peel strength of from 2 to 6 g (e.g. about 5 g).

The non-tacky silicones which are used in the dressings of the present invention preferably display a Shore A hardness of less than 5, and more preferably less than 2. Particularly preferred are silicones having a Shore A hardness of less than 1, and most preferable are gels having no measurable Shore A hardness.

The crosslinked silicones may be formed from linear silicones having reactive groups thereon, as is known in the art. The reactive groups which cause the crosslinking reaction may be silanol groups. Such groups will react with other silanol groups in the presence of a suitable catalyst (such as stannous octoate) or heat, or both, with the elimination of water. Preferably, however, the gels are formed by reaction between a vinyl-substituted silicone and a hydride-containing silicone in the presence of a suitable catalyst such as a platinum catalyst.

The starting silicones may have a number average molecular weight in the range 5000 to 200,000, and may, for example, have from 0.004 to 0.4 mmoles reactive group/g. Preferably, the number average molecular weight is from 10,000 to 100,000, and from 0.01 to 0.2 mmoles reactive group are present /g of silicone for example, a starting silicone composition having an average molecular weight of 10,000 would comprise 0.1 mmoles of said silicone composition per gram and may contain up to 0.2 mmoles of a reactive group, thus in this example each molecule would have two reactive groups or sites.

When the silicones are formed by crosslinking a mixture of two or more silicones, the molecular weights of the various components and/or their degree of substitution by reactive groups may be different. This allows gels having different physical properties to be formed merely by varying the proportions of the components.

For example, a tacky gel can be formed by using a relatively high proportion of high molecular weight, hydride-containing component and a relatively low proportion of a low molecular weight, vinyl-substituted component. The hydride-containing component may constitute from 50% to 90% by weight of the starting materials, and preferably from 60% to 80%, for example 70% by weight, the balance being the vinyl-substituted component. Conversely, a silicone gel which is dry and non-tacky to the touch may be formed by using a relatively high proportion of the same vinyl-substituted component, and a lower proportion of the hydride-containing vinyl-substituted component. For example, such gels may be formed from mixtures containing from 50% to 90% by weight of the component, and preferably from 60% to 80%, for example 70% by weight, the balance being the hydride-containing component.

When two components of different molecular weight are employed, the larger molecular weight component preferably has a number average molecular weight in the range 25,000 to 70,000, and it preferably has from 0.05 to 0.2 mmoles reactive group (e.g. hydride groups) /g. More preferably, the larger molecular weight component has a number average molecular weight in the range 40,000 to 45,000 (generally corresponding to a viscosity of from 1500 to 1700 mPas), and has from 0.07 to 0.13 mmoles reactive group/g.

The smaller molecular weight component preferably has a number average molecular weight in the range 10,000 to 25,000, and it preferably has from 0.01 to 0.025 mmoles reactive group (e.g. vinyl groups)/g. More preferably, the smaller molecular weight component has a number average molecular weight in the range 16,000 to 20,000 (generally corresponding to a viscosity of from 400 to 600 mPas), and has from 0.016 to 0.018 mmoles reactive group/g.

If the crosslinked silicones for use in the present invention are to be formed from vinyl-substituted and hydride-containing poly(dimethylsiloxanes), it is preferred that the hydride groups be present in at least a four-fold excess over the vinyl groups in a mixture of equal parts by weight of the starting materials.

The components for forming suitable crosslinked silicones for use in the dressings of the present invention are available from Bayer (UK) Limited, England, under the references VP AC 3293 (A) and VP AC 3293 (B). These are vinyl-substituted and hydride-containing poly(dimethylsiloxanes), respectively.

The dressings of the present invention are formed by coating a sheet of apertured material with a non-crosslinked silicone material and then causing it to crosslink. In the case of gels formed by reacting vinyl groups of one component with hydride groups of the other component, such curing will generally be carried out in the presence of a catalyst such as a platinum complex at a concentration of from 5 to 15 ppm. In such a case, the gel may be cured at room temperature over a period of several days, but elevated temperatures are preferably employed. For example, the silicone gels may be cured at a temperature of from 40° to 120° C. and preferably at a temperature between 80° and 100° C. At a temperature of 80° C., curing will generally take from 10 seconds to 10 minutes, for example from 1 to 5 minutes. At a temperature of 50° C., curing will generally taken from 10 minutes to 2 hours, for example from 15 minutes to 1 hour.

Tacky gels will generally be coated onto the gauze at a weight of from $70 g/m^2$ to $700 g/m^{2'1}$, preferably from $200 g/m^2$ to $600 g/m^2$, and more preferably from $300 g/m^2$ to $400 g/m^2$.

Non-tacky crosslinked silicones will preferably be applied at a weight of from 20 to 700 $g/m^2$, more preferably at a weight of from 50 to 250 $g/m^2$, and most preferably at a weight of from 100 to 160 $g/m^2$.

The apertured material which forms the substrate for the silicone coating may, if desired, be an apertured plastics film. Alternatively, it may, for example, be a woven or non-woven or knitted mesh, such as a cotton gauze. The effectiveness with which silicone elastomers can encapsulate the fibres of a fabric means that low quality, inexpensive fabrics may be used without sacrificing the quality of the resultant dressing. Moreover, the effectiveness of encapsulation by silicone elastomers means that the apertured material may be printed or dyed with decorative or informative matter with little danger of the ink or dye being released into the wound to which the dressing is applied.

Fabrics having a weight of from 15 to 200 g/m$^2$ are generally found to be suitable for use in the dressings of the invention, and fabrics weighing from 40 to 100 g/m$^2$ are preferred. Particularly preferred embodiments employ a fabric of from 50 to 90 g/m$^2$ when the silicone is a tacky gel, and from 90 to 100 g/m$^2$ when the silicone is non-tacky.

The size and shape of the apertures in the apertured material are not critical, but the apertures should be such as to to ensure that the material can be adequately coated with silicone gel without them becoming occluded. The apertures generally have an aspect ratio of from 1:1 to 5:1, and preferably from 1:1 to 2:1. For example, the apertures may be approximately circular or approximately square. The apertures preferably have an average diameter of from 0.3 to 4 mm, and more preferably from 0.5 to 2 mm. In the case of dressings have non-tacky coatings the apertures most preferably have an average diameter of from 0.6 to 1.0 mm.

According to a further aspect of the present invention, there is provided a dressing comprising one or more layers of support material, such as the apertured material described above, coated with a tacky gel on one surface and a non-tacky elastomer on the other surface. Such a dressing has the advantage of being convenient to use, in that it will readily remain in position while being secured with a bandage, and it has the further advantage of being non-tacky on the surface which may come into contact with the wearer's clothing. This type of dressing may be formed by first coating a layer of gauze with a relatively small amount of a composition for forming a non-tacky silicone elastomer (for example, from 20g/m$^2$ to 150g/m$^2$), followed by curing, and then applying a coating of a composition for forming a tacky silicone gel (e.g. at a weight of from 60g/m$^2$ to 350g/m$^2$), followed by further curing.

In an alternative method, two sheets of support material are coated separately, one with a composition for forming a tacky silicone gel and the other with a composition for forming a non-tacky silicone elastomer. The two coated layers are then superimposed, either before or after curing of the silicone compositions. If the two layers are superimposed after curing of their respective coatings, the layers may be caused to adhere to each other either by means of a suitable adhesive or by means of a further layer of a crosslinkable silicone composition which is then cured.

The dressings of the present invention may be provided with an absorbent pad to absorb exudate which passes through the gel-coated material. Such absorbent pads may be of conventional construction, and may be formed from materials such as cellulose fibres, superabsorbents and hydrophilic (e.g. polyurethane) foams.

The dressings may be secured to the user in any convenient manner, such as by conventional bandages or adhesive tape.

Generally, wound dressings according to the invention will be sterilized (e.g. by $\gamma$-radiation) and sealed in a bacteria-proof envelope.

While the silicone coated materials according to the present invention are particularly suitable for use as wound dressings, it will be appreciated that other applications for them exist. For example, they are useful in providing cushioning and protection from abrasions and blisters, for use by athletes, and in the prevention of pressure-sores in bed-ridden patients. Those dressings in which one surface is tacky and the other non-tacky are especially suitable for use in the latter applications, in which the user's clothing (rather than a bandage) is likely to come into contact with the outer surface of the dressing.

The dressings of the present invention are further illustrated by the following examples.

EXAMPLE 1

A 10 cm square piece of knitted cotton fabric (90 g/m$^2$, mesh size 0.5 mm$^2$) was coated on both surfaces with a mixture comprising 70% by weight VP AC 3293 (B) (the hydride-containing poly(dimethylsiloxane), from Bayer), and 30% by weight VP AC 3293 (A) (the vinyl-substituted poly(dimethylsiloxane), also from Bayer) The mixture further contained approximately 10 ppm of platinum as a platinum complex. The weight of silicone material applied was 400 g/m$^2$. The silicone was then cured for 2 minutes at 80° C., and allowed to cool. The resultant gel was tacky to the touch, but remained firmly attached to the gauze. The dressing was eminently suitable for use in place of a conventional tulle gras dressing.

EXAMPLE 2

Example 1 was repeated, except that the gel was formed from a mixture of 30% by weight VP AC 3293 (B) and 70% by weight VP AC 3293 (A), and the coating weight was 150 g/m$^2$. The gel was dry and non-tacky to the touch, and the dressing was admirably suited to be used in place of a conventional non-adherent dressing such as Johnson & Johnson's N-A (Trade Mark) dressing.

EXAMPLE 3

The gauze of Example 1 was coated on one surface with 50 g/m$^2$ of the silicone mixture described in Example 2. After curing, the other surface of the gauze was coated with 80 g/m$^2$ of the silicone mixture described in Example 1. After further curing, the dressing had one tacky and one non-tacky surface.

It will, of course, be understood that the present invention has been described above purely by way of example, and modifications of detail can be made within the scope of the invention.

We claim:

1. A liquid permeable wound dressing which is non-adherent to wounds comprising one or more sheets of apertured liquid permeable material coated with a sufficient amount of cross-linked tacky silicone gel to effectively encapsulate the one or more sheets of apertured liquid permeable material but insufficient to occlude the apertures therein.

2. A dressing according to claim 1 wherein the gel has a peel strength of from 5 to 100 g.

3. A dressing according to claim 1 wherein the gel has a tensile strength of from 50 to 400 g.

4. A dressing according to claim 1 wherein the gel has a penetrability of from 5 to 50 mm.

5. A dressing according to claim 1 wherein the weight of gel present is from 70 to 700 g/m² of apertured material.

6. A dressing according to claim 1 wherein the apertured material is a woven, nonwoven or knitted mesh.

7. A dressing according to claim 1 comprising one or more layers of support material, wherein each layer has two surfaces having a tacky silicone gel coating on one surface thereof and, a non-tacky silicone elastomer coating on the other surface.

8. A dressing according to claim 7 wherein the tacky silicone gel has a peel strength of from 5 to 100 g., and a tensile strength of from 50 to 400 g. and a penetrability of from 5 to 50 mm. and is present in an amount by weight from 70 to 700 g./m² of the apertured material; and the non-tacky silicone elastomer has a peel strength of from 0 to 15 g. and a tensile strength of from 100 to 600 g. and a penetrability of from 1 to 10 mm. and is present in an amount by weight from 20 to 700 g./m² of the apertured material.

9. A method of forming a wound dressing which is non-adherent to wounds comprising coating one or more sheets of apertured material with an amount of silicone gel precursor which is sufficient to effectively encapsulate the one or more sheets of apertured material, but insufficient to occlude the apertures therein, and curing said precursor to form gel.

10. A method according to claim 9 wherein said silicone gel precursor comprises a mixture of vinylsubstituted poly(dimethylsiloxane) and hydridecontaining poly(dimethylsiloxane).

* * * * *

UNITED STATES PATENT AND TRADEMARK OFFICE
CERTIFICATE OF CORRECTION

PATENT NO. : 4,838,253

DATED : June 13, 1989

INVENTOR(S) : Nigel J. Brassington, John A. Gilbert

It is certified that error appears in the above-identified patent and that said Letters Patent is hereby corrected as shown below:

column 8, line 11: before the word "gel" insert the words --a silicone--.

Signed and Sealed this

Twenty-seventh Day of February, 1990

Attest:

JEFFREY M. SAMUELS

Attesting Officer

Acting Commissioner of Patents and Trademarks